US012594111B2

(12) United States Patent
Sprain et al.

(10) Patent No.: US 12,594,111 B2
(45) Date of Patent: Apr. 7, 2026

(54) HIGH PRESSURE, LOW TEMPERATURE COUPLING

(71) Applicant: BTG International Limited, London (GB)

(72) Inventors: Jason Sprain, Shoreview, MN (US); Mark Timothy Johnson, Mounds View, MN (US); Maciej Wojciech Misiak, Eden Prairie, MN (US); Andrew Kevin Zachman, St. Michael, MN (US)

(73) Assignee: BTG International Limited, London (GB)

( * ) Notice: Subject to any disclaimer, the term of this patent is extended or adjusted under 35 U.S.C. 154(b) by 329 days.

(21) Appl. No.: 18/083,195

(22) Filed: Dec. 16, 2022

(65) Prior Publication Data

US 2023/0190356 A1     Jun. 22, 2023

Related U.S. Application Data

(60) Provisional application No. 63/290,777, filed on Dec. 17, 2021.

(51) Int. Cl.
*F16L 51/00*     (2006.01)
*A61B 18/02*     (2006.01)
(Continued)

(52) U.S. Cl.
CPC .............. *A61B 18/02* (2013.01); *F16L 51/00* (2013.01); *A61B 2018/00172* (2013.01); *A61B 2018/00577* (2013.01); *F16L 37/407* (2013.01)

(58) Field of Classification Search
CPC .......... A61B 18/02; A61B 2018/00172; A61B 2018/00577; A61B 2018/00041;
(Continued)

(56) References Cited

U.S. PATENT DOCUMENTS 4,123,092 A * 10/1978 Colbert, Jr. ............. F16L 51/00
                                                                          285/302
7,913,716 B2    3/2011 Oestergaard et al.
(Continued)

FOREIGN PATENT DOCUMENTS

JP          499784          3/1974
JP       2000274563        10/2000
(Continued)

OTHER PUBLICATIONS

"International Preliminary Report on Patentability," for PCT Patent Application No. PCT/US2022/053239 mailed Jun. 27, 2024 (7 pages).
(Continued)

*Primary Examiner* — Ankit D Tejani
*Assistant Examiner* — Joshua Brendon Solomon
(74) *Attorney, Agent, or Firm* — Pauly, DeVries Smith & Deffner, LLC

(57)          ABSTRACT

Disclosed herein are devices, systems, and method for multi-stage, reusable coupling. Such a coupler can have a formable flow path and can include a first sealing engagement and a second sealing engagement. The first sealing engagement can be configured to provide a first seal of the coupler at a first temperature condition. The second sealing engagement can be configured to provide a second seal of the coupler at a second temperature condition that is different from the first temperature condition.

18 Claims, 9 Drawing Sheets

(51) Int. Cl.
    *A61B 18/00*         (2006.01)
    *F16L 37/407*     (2006.01)

(58) Field of Classification Search
    CPC .... A61B 2018/0212; A61B 2018/0262; A61B
               2018/0293; A61B 2017/00477; A61B
               2090/374; A61B 90/37; F16L 51/00;
               F16L 37/407; F16J 15/068; F16J 15/002
    See application file for complete search history.

(56)             References Cited

U.S. PATENT DOCUMENTS

| | | | |
|---|---|---|---|
| 2008/0110182 A1 | 5/2008 | Vancelette et al. | |
| 2011/0225988 A1* | 9/2011 | Baust .................... | F16L 13/103 |
| | | | 62/50.7 |

| | | | |
|---|---|---|---|
| 2015/0297279 A1* | 10/2015 | Clarke .................. | A61B 18/02 |
| | | | 606/22 |
| 2021/0102629 A1 | 4/2021 | Edwards | |

FOREIGN PATENT DOCUMENTS

| | | |
|---|---|---|
| JP | 2008151268 | 7/2008 |
| WO | 2023114513 | 6/2023 |

OTHER PUBLICATIONS

"International Search Report and Written Opinion," for PCT Patent Application No. PCT/US2022/053239 mailed Apr. 17, 2023 (10 pages).

"Response to Rule 161 Communication," for European Patent Application No. 22854222.1 filed Jan. 16, 2025 (14 pages).

"First Office Action," for Japanese Patent Application No. 2024-536221 mailed Jun. 24, 2025 (9 pages) with English translation.

* cited by examiner

310

330

316a

314

322

312

316

324

320

220

HIGH PRESSURE, LOW TEMPERATURE COUPLING

CROSS REFERENCE TO RELATED APPLICATION

This application claims priority to Provisional Application No. 63/290,777, filed Dec. 17, 2021, which is herein incorporated by reference in its entirety.

TECHNICAL FIELD

The present disclosure relates to coupling devices, systems, and method, and in particular, a sealing engagement that is suitable for coupling a source of cryomedia to a cryogenic tool.

BACKGROUND

Cryoablation of tissues has become an increasingly popular method of treatment for a variety of pathological conditions. Malignancies in body organs such as the breast, lung, prostate, kidney, liver and other organs are successfully treated by cryoablation, as well as a variety of non-malignant pathological conditions and certain cases of chronic pain may also be treated through cryosurgery.

SUMMARY

Disclosed herein are couplers with multi-stage sealing. Such couplers are particularly useful in applications where there is dynamic temperature change within operating parameters. For instance, an illustrative coupler can be useful for connecting a source of pressurized cryomedia to a cryosurgical tool, a male connector for connection to a female connector, a female connector for connection to a male connector, a cryosurgery system and a method of coupling a source of cryomedia to a cryogenic tool.

In an example ("Example 1"), a coupler with a formable flow path is disclosed. The coupler can include a first sealing engagement and a second sealing engagement. The first sealing engagement can be configured to provide a first seal of the coupler at a first temperature condition. The second sealing engagement can be configured to provide a second seal of the coupler at a second temperature condition that is different from the first temperature condition.

According to another example ("Example 2") further to Example 1, the coupler can include a first connector and a second connector. The formable flow path can be formable via coupling of the first connector with the second connector. In this regard, a working media can be allowed to flow through the flow path.

According to another example ("Example 3") further to any of the preceding examples, at least one of the first and second sealing engagements can be provided between complementary surfaces of the first and second connectors and, optionally, the first connector can have a first coefficient of thermal expansion with the second connector having a second coefficient of thermal expansion that is different from the first coefficient of thermal expansion.

According to another example ("Example 4") further to Example 3, the first sealing engagement can be provided between first complimentary surfaces of the first and second connectors, and the second sealing engagement can be provided between second complementary surfaces of the first and second connectors, and where, optionally, a resilient seal is optionally provided between the second complementary surfaces.

According to another example ("Example 5") further to any of the preceding examples, wherein the first connector is configured to receive the second connector such that under the first temperature condition an exterior surface of the first connector engages an interior surface of the second connector so as to form at least one of the first and sealing engagements.

According to another example ("Example 6") further to any of the preceding examples, the first temperature condition can include a first range of temperatures, and the second temperature condition can include a second range of temperatures that is different from the first range of temperatures, and optionally where at least one of: the first range of temperatures is lower than the second range of temperatures, the first range of temperatures has minimal overlap with the second range of temperatures, and the first range of temperatures includes cryogenic temperatures.

In another Example ("Example 7"), a cryosurgery system is disclosed. The cryosurgery system can include a cryosurgical tool having a cryogenic media supply conduit and a source of cryogenic media having a cryogenic media feed conduit connectable to the cryogenic media supply conduit via a coupler. The coupler can include a first sealing engagement and a second sealing engagement. The first sealing engagement can be configured to provide a first seal of the coupler at a first temperature condition. T second sealing engagement can be configured to provide a second seal of the coupler at a second temperature condition that is different from the first temperature condition.

According to another example ("Example 8") further to Example 7, the coupler can include a first connector and a second connector, and optionally where a flow path of the coupler is formable via engagement of the first connector with the second connector. In this regard, the flow path can be configured to receive the cryogenic media from the cryogenic media supply conduit.

According to another example ("Example 9") further to Examples 7 and 8, the first temperature condition can include a first range of temperatures that includes cryogenic temperatures such that the first sealing engagement is formed at the cryogenic temperatures, and optionally where the cryosurgery system includes a heater that is configured to heat a portion of at least one of the first connector and the second connector. In this regard, the coupler can be configured to be thawed to release the first sealing engagement with operation of the heater.

According to another example ("Example 10") further to any of Examples 7 to 9, the first connector can have a first coefficient of thermal expansion, and the second connector can have a second coefficient of thermal expansion that is different from the first coefficient of thermal expansion, and where optionally the first coefficient of thermal expansion and the second coefficient of thermal expansion are selected such that cooling causes first complementary surfaces of the first and second connectors to form a the first sealing engagement and/or the second sealing engagement is provided by a resilient seal arranged between second complementary surfaces of the first and second connectors.

According to another example ("Example 11") further to Example 10, wherein the first connector comprises a first fluid conduit and the second connector comprises a second fluid conduit, and wherein the cryosurgery system further comprises a clamp for securing the first and second connectors in a fluid-tight arrangement such that the first conduit is in fluid communication with the second conduit and a clamp locator for locating the clamp such that the first and second connectors are aligned.

In yet another Example ("Example 12"), a method of coupling a source of cryogenic fluid to a cryosurgical tool using a coupler is disclosed. The method can include sealing the coupler with a first seal via a first sealing engagement that is configured to provide the first seal of the coupler at a first temperature condition. The method can include sealing the coupler with a second seal via a second sealing engagement that is configured to provide the second seal of the coupler at a second temperature condition that is different from the first temperature condition.

According to another example ("Example 13") further to Example 12, sealing the coupler with the first seal via the first sealing engagement that is configured to provide the first seal of the coupler at the first temperature condition can include allowing first complementary surfaces of first and second connectors to move into sealing engagement, and optionally where the first connector has a first coefficient of thermal expansion and the second connector has a second coefficient of thermal expansion that is different from the first coefficient of thermal expansion.

According to another example ("Example 14") further to Example 13, sealing the coupler with the second seal via the second sealing engagement that is configured to provide the second seal of the coupler at the second temperature condition that is different from the first temperature condition can include forming a fluidic seal between second complementary surfaces of the first and second connectors.

According to another example ("Example 15") further to any of Examples 12 to 14, where the method includes clamping the first and second connectors in a fluid-tight arrangement such that a first conduit of the first connecter is in fluid communication with a second conduit of the second connector.

In yet another Example ("Example 16"), a coupler with a formable flow path is disclosed. The coupler can include a first sealing engagement and a second sealing engagement. The first sealing engagement can be configured to provide a first seal of the coupler at a first temperature condition. The second sealing engagement can be configured to provide a second seal of the coupler at a second temperature condition that is different from the first temperature condition.

According to another example ("Example 17") further to Example 16, the coupler can include a first connector and a second connector, where optionally the formable flow path is formable via coupling of the first connector with the second connector such that a working media is allowed to flow through the flow path and the first and second temperature conditions correspond to the flow of the working media through the flow path.

According to another example ("Example 18") further to Example 17, the first sealing engagement can be provided between first complementary surfaces of the first and second connectors.

According to another example ("Example 19") further to Example 18, the second sealing engagement can be provided between second complementary surfaces of the first and second connectors.

According to another example ("Example 20") further to Example 18, a resilient seal can be provided between the second complementary surfaces.

According to another example ("Example 21") further to Example 17, the first connector can be configured to receive the second connector such that under the first temperature condition an exterior surface of the first connector engages an interior surface of the second connector so as to form the first sealing engagement.

According to another example ("Example 22") further to Example 16, the first temperature condition can include a first range of temperatures, and the second temperature condition can include a second range of temperatures that is different from the first range of temperatures.

According to another example ("Example 23") further to Example 22, at least one of: the first range of temperatures is lower than the second range of temperatures and the first range of temperatures has minimal overlap with the second range of temperatures.

According to another example ("Example 24") further to Example 23, the first range of temperatures can include cryogenic temperatures.

According to another example ("Example 25") further to Example 17, the first connector can have a first coefficient of thermal expansion, and optionally the second connector has a second coefficient of thermal expansion that is different from the first coefficient of thermal expansion.

According to another example ("Example 26") further to Example 16, the first connector can be coupleable to the second connector via a clamping force such that the formable flow path is configured to withstand high-pressure operating conditions.

In yet another Example ("Example 27"), a cryosurgery system is disclosed. The cryosurgery system can include a cryosurgical tool having a cryogenic media supply conduit and a source of cryogenic media having a cryogenic media feed conduit connectable to the cryogenic media supply conduit via a coupler. The coupler can include a first sealing engagement and a second sealing engagement. The first sealing engagement can be configured to provide a first seal of the coupler at a first temperature condition. The second sealing engagement can be configured to provide a second seal of the coupler at a second temperature condition that is different from the first temperature condition.

According to another example ("Example 28") further to Example 26, the coupler can include a first connector and a second connector; and optionally where a flow path of the coupler is formable via engagement of the first connector with the second connector, the flow path being configured to receive the cryogenic media from the cryogenic media supply conduit.

According to another example ("Example 29") further to Example 29, where the first temperature condition comprises a first range of temperatures that includes cryogenic temperatures such that the first sealing engagement is formed at the cryogenic temperatures; and wherein the cryosurgery system further comprises a heater that is configured to heat a portion of at least one of the first connector and the second connector such that the coupler is configured to be thawed to release the first sealing engagement with operation of the heater.

According to another example ("Example 30") further to Example 28, wherein the first connector has a first coefficient of thermal expansion, and the second connector has a second coefficient of thermal expansion that is different from the first coefficient of thermal expansion; wherein the first coefficient of thermal expansion and the second coefficient of thermal expansion are selected such that cooling causes first complementary surfaces of the first and second connectors to form a the first sealing engagement; and wherein the second sealing engagement is provided by a resilient seal arranged between second complementary surfaces of the first and second connectors.

According to another example ("Example 31") further to Example 28, wherein the first connector comprises a first fluid conduit and the second connector comprises a second fluid conduit, and wherein the cryosurgery system further comprises a clamp for securing the first and second connectors in a fluid-tight arrangement such that the first conduit is in fluid communication with the second conduit and a clamp locator for locating the clamp such that the first and second connectors are aligned.

In still yet another example ("Example 32") a method of coupling a source of cryogenic fluid to a cryosurgical tool using a coupler is disclosed. The method can include sealing the coupler with a first seal via a first sealing engagement that is configured to provide the first seal of the coupler at a first temperature condition. The method can include sealing the coupler with a second seal via a second sealing engagement that is configured to provide the second seal of the coupler at a second temperature condition that is different from the first temperature condition.

According to another example ("Example 33") further to Example 32, sealing the coupler with the first seal via the first sealing engagement that is configured to provide the first seal of the coupler at the first temperature condition can include allowing first complementary surfaces of first and second connectors to move into sealing engagement, where optionally the first connector has a first coefficient of thermal expansion and the second connector has a second coefficient of thermal expansion that is different from the first coefficient of thermal expansion.

According to another example ("Example 34") further to Example 33, sealing the coupler with the second seal via the second sealing engagement that is configured to provide the second seal of the coupler at the second temperature condition that is different from the first temperature condition can include forming a fluidic seal between second complementary surfaces of the first and second connectors.

According to another example ("Example 35") further to Example 34, further comprising clamping the first and second connectors in a fluid-tight arrangement such that a first conduit of the first connecter is in fluid communication with a second conduit of the second connector.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

6

Figure 1:
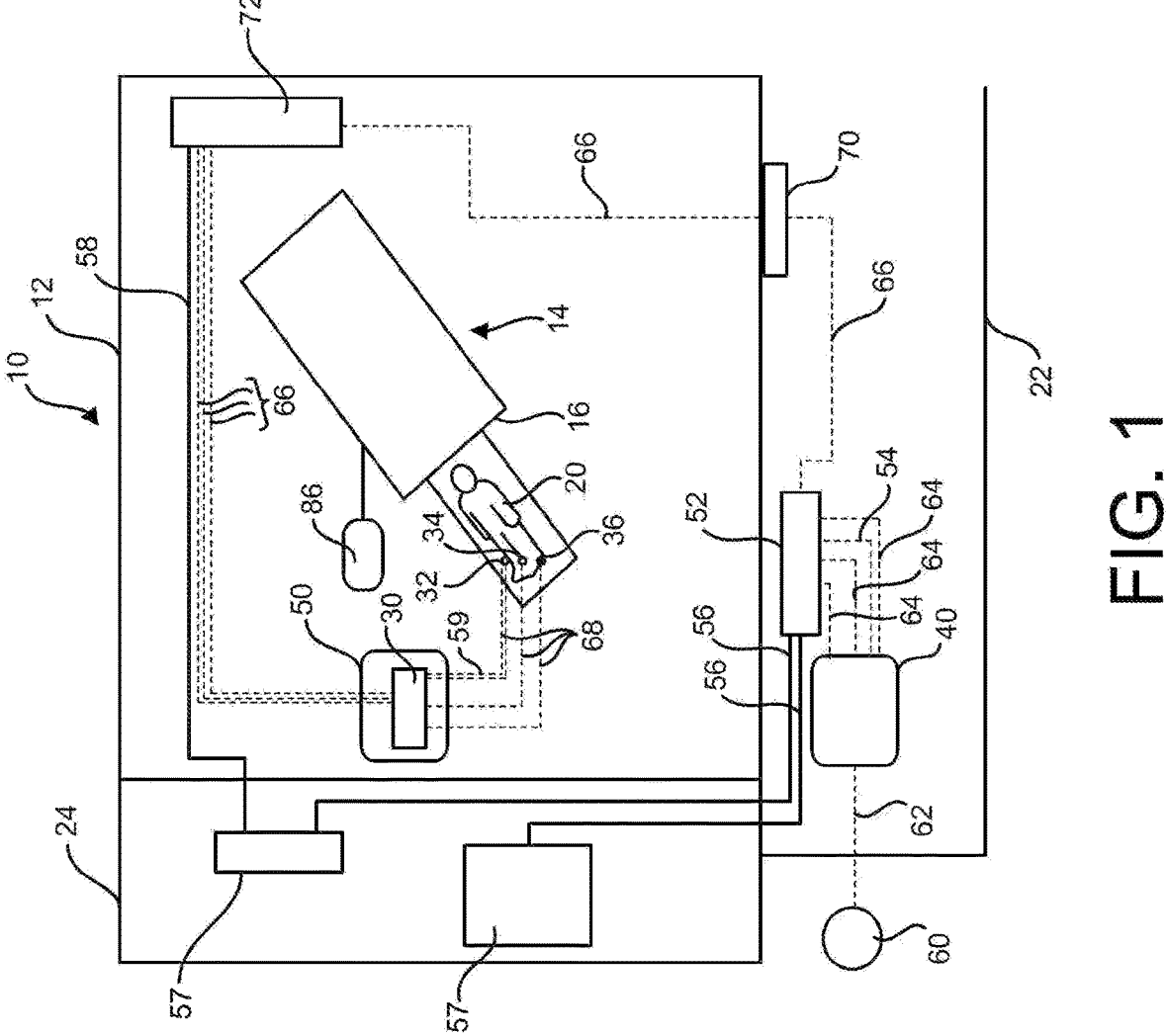
FIG. 1 is a schematic of a Magnetic Resonance Imaging-guided cryosurgery system, according to principles of the present disclosure.
Figure 3:
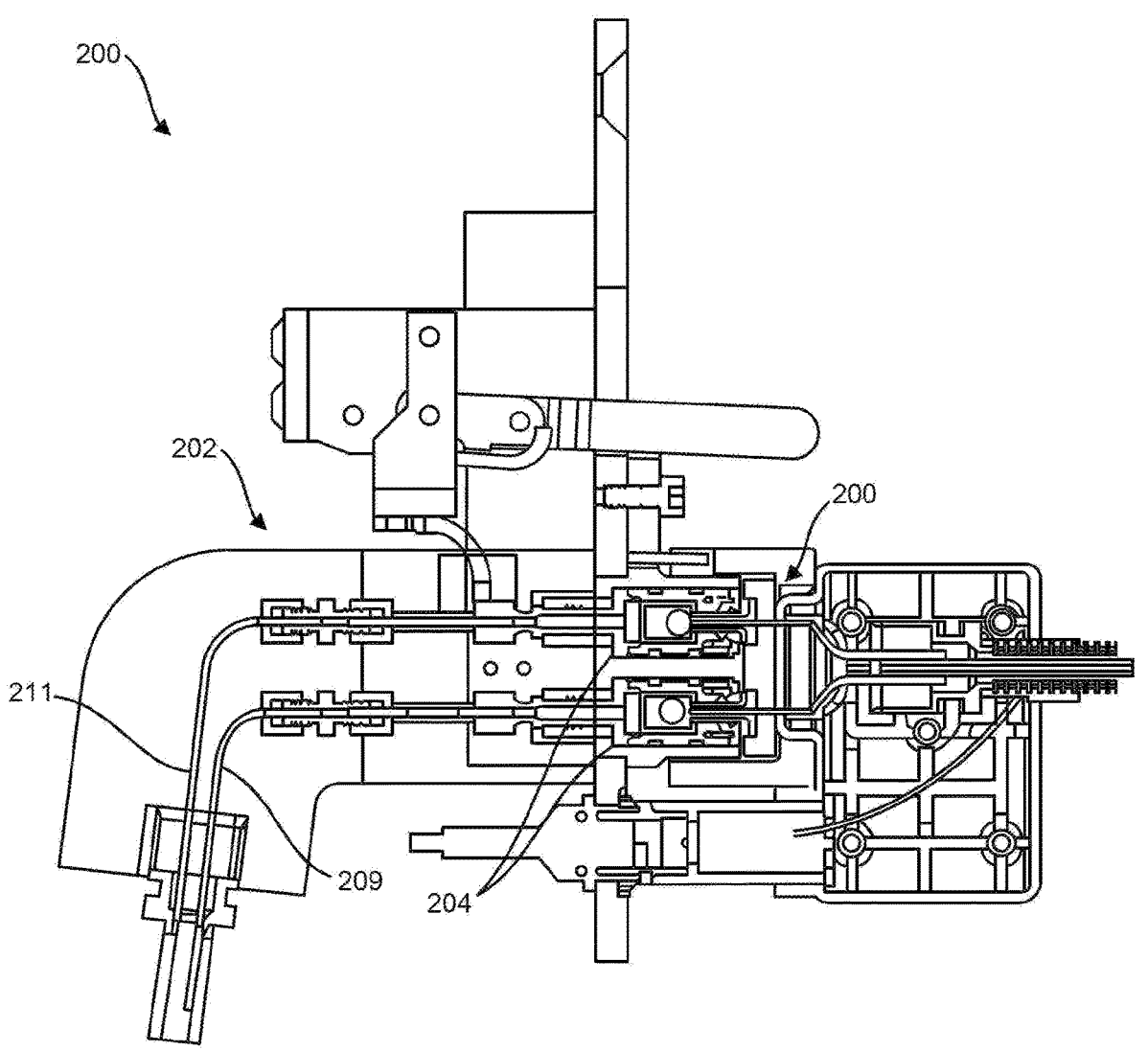
FIG. 3 is a sectional plan view of a portion of a connection interface permitting connection of the cryoprobe of FIG. 2A.
Figure 3A:
FIG. 3A is a schematic plan view of a coupler, according to principles of the present disclosure.
Figure 3B:
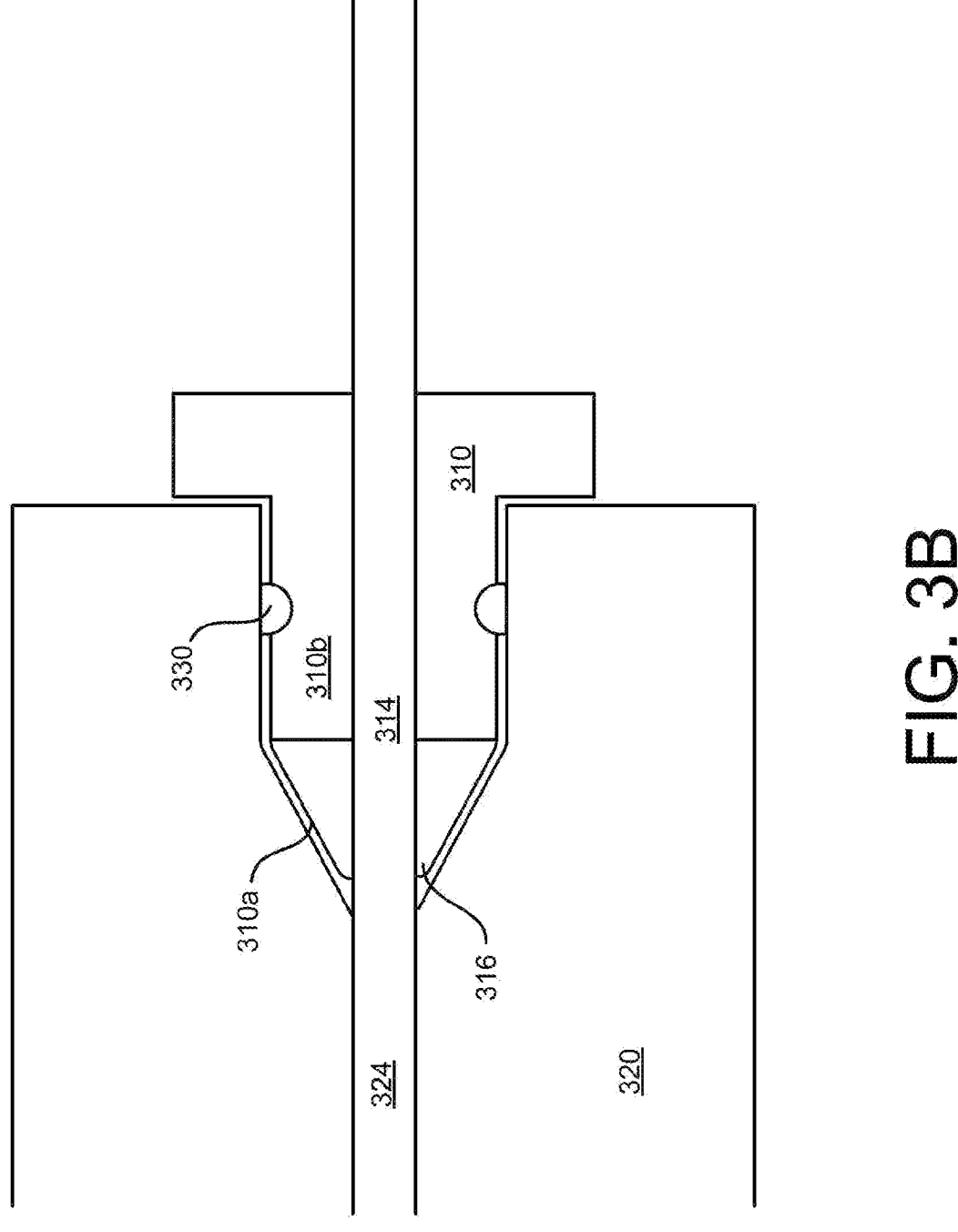
FIG. 3B is a schematic plan view of a coupler with multi-piece connectors according to principles of the present disclosure.
Figure 3C:
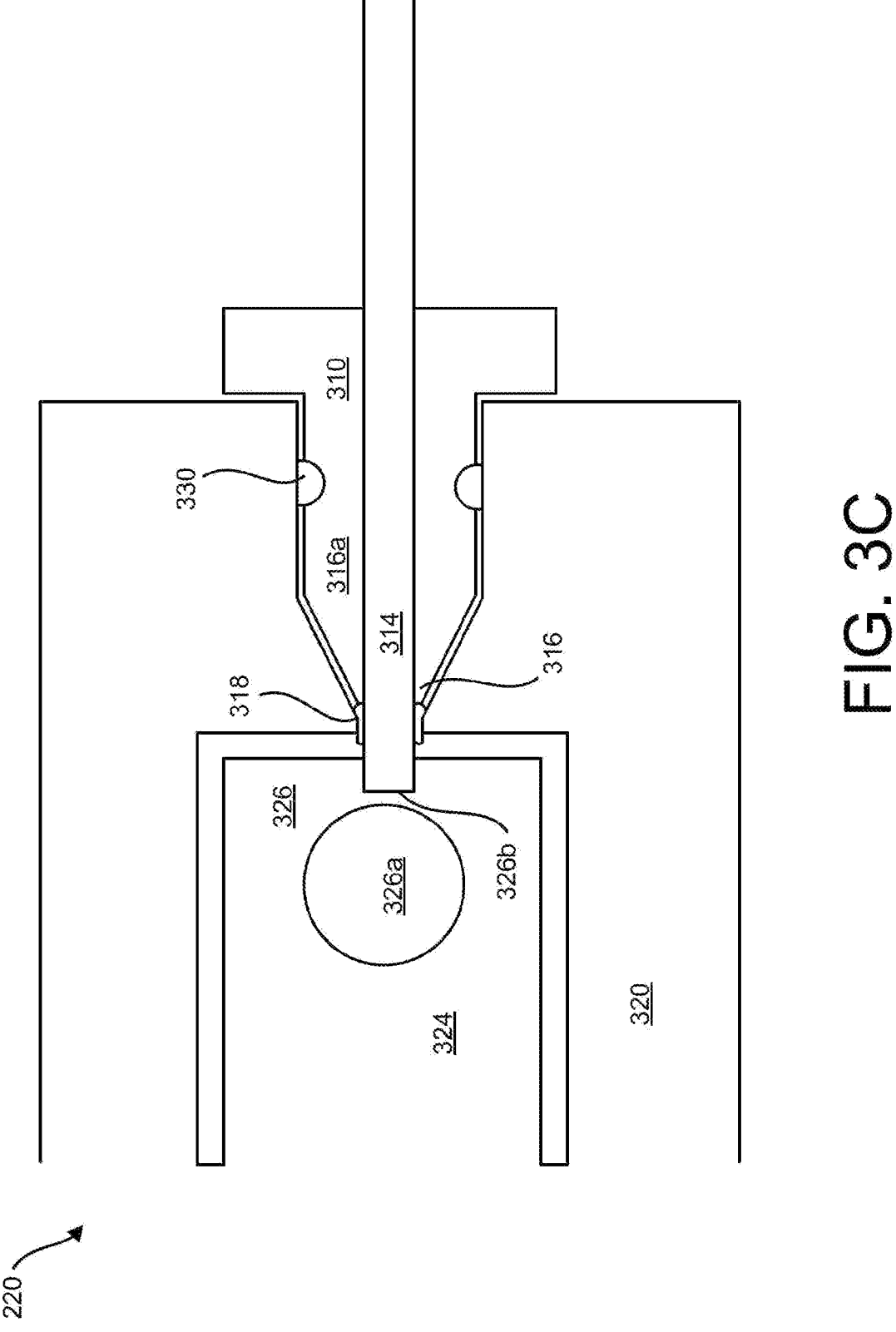
FIG. 3C is a schematic plan view of a coupler with a connected valve, according to principles of the present disclosure.
Figure 3D:
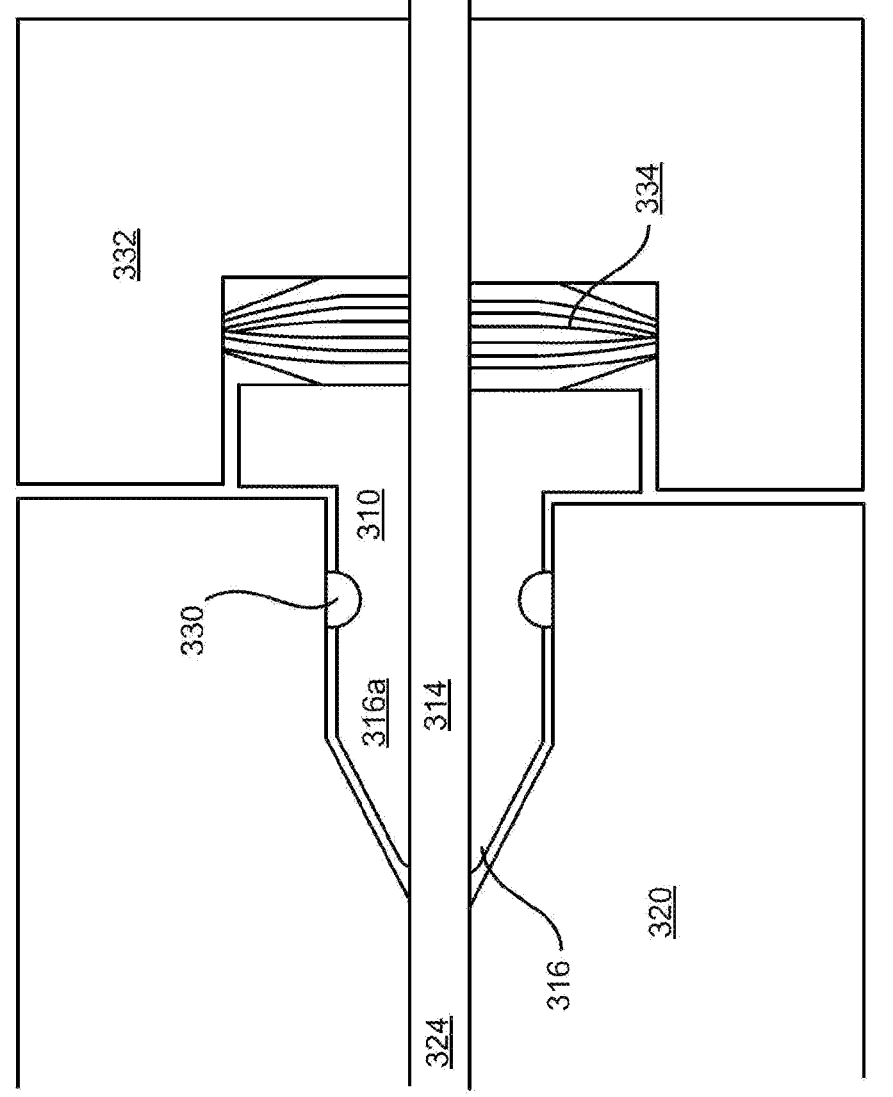
Figure 3D:
Figure 3E:
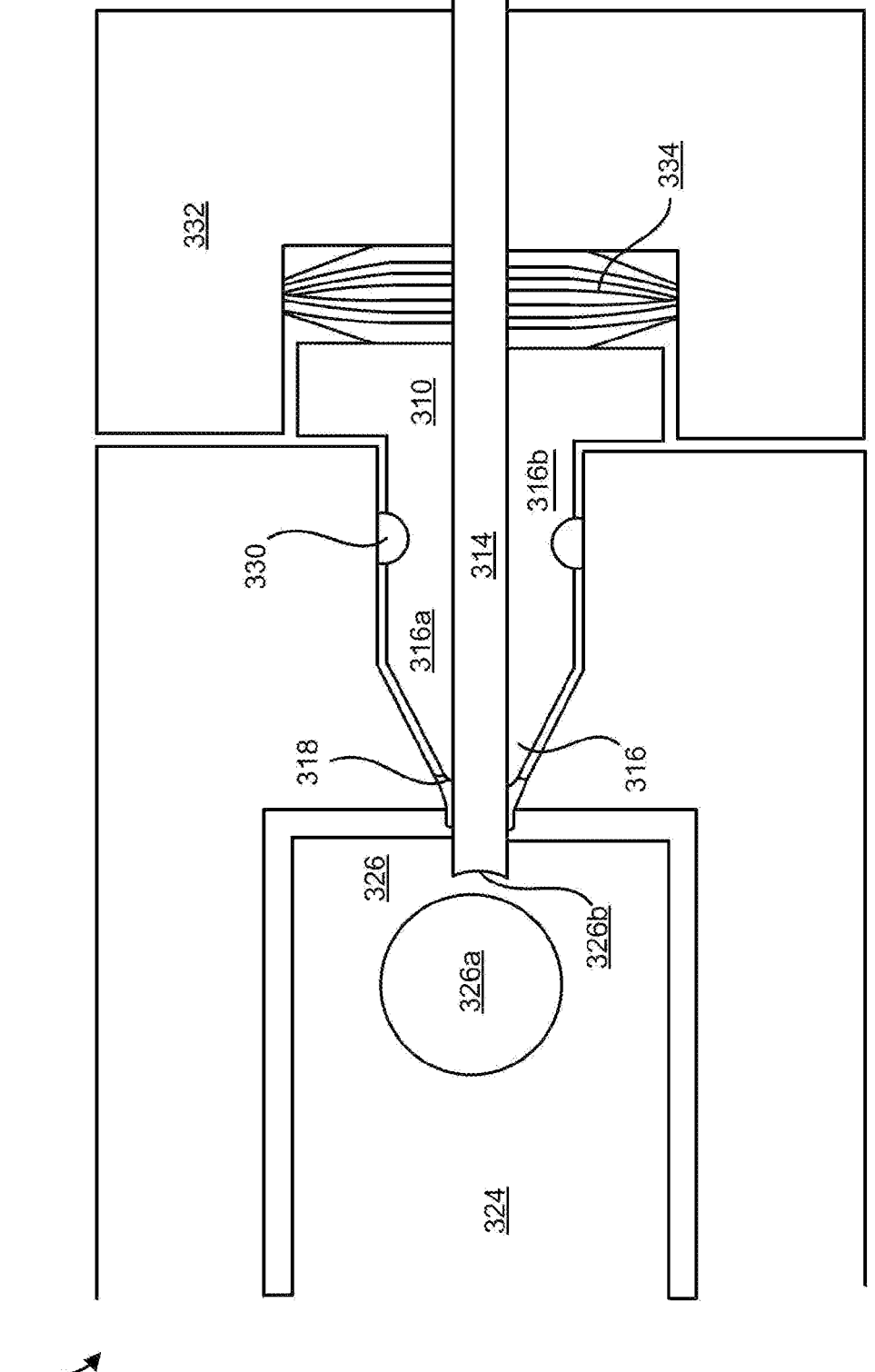
Figure 4:
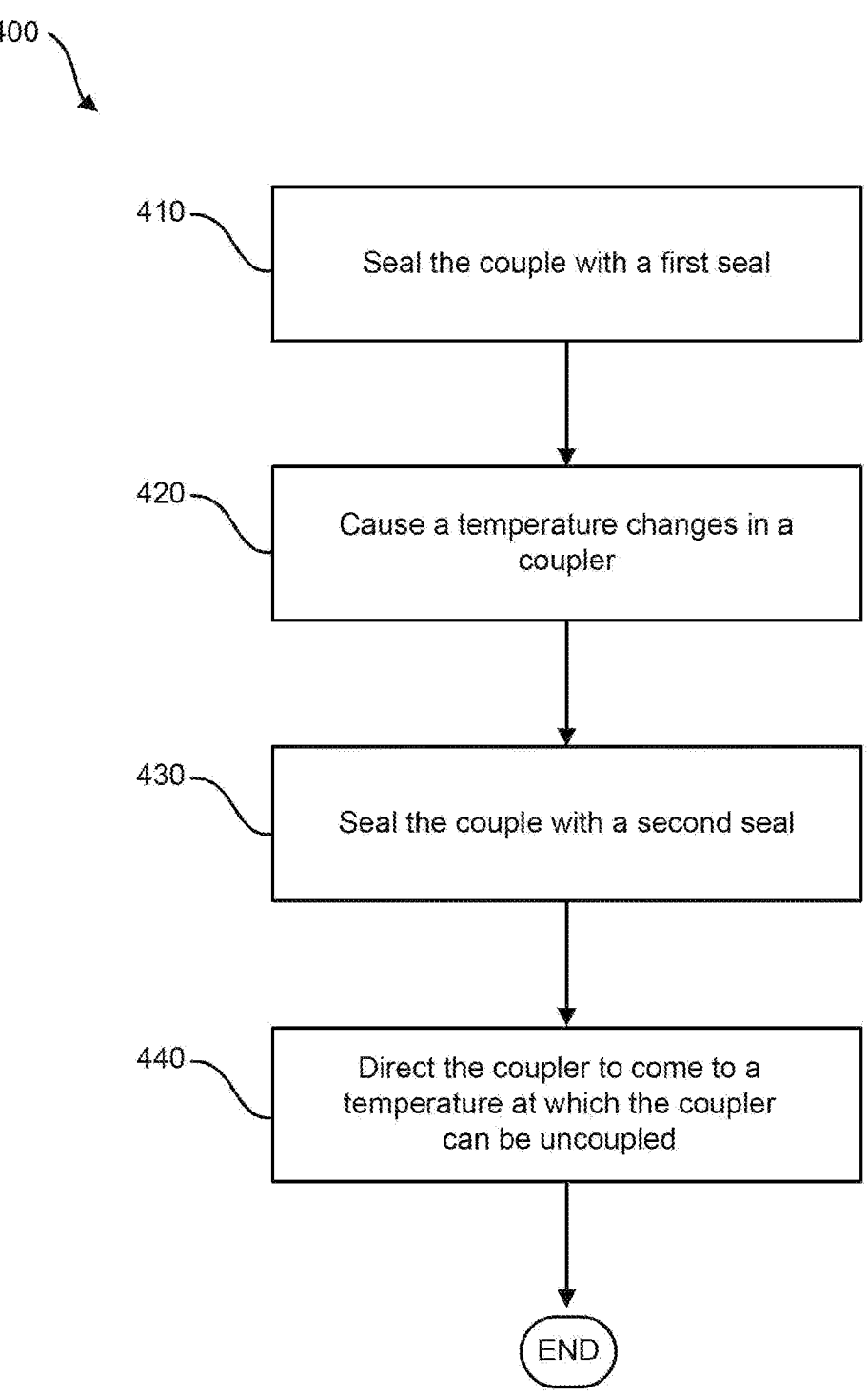

FIG. 3D is a schematic plan view of the coupler in FIG. 1 with a clamp to secure connectors of the coupler, according to principles of the present disclosure;

FIG. 3E is a schematic plan view of the coupler in FIG. 3 with a clamp to secure connectors of the coupler, according to principles of the present disclosure; and FIG. 4 is a flowchart of a method for coupling surgical tools, according to principles of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Principles of the present disclosure will be discussed here below in relation to cryosurgery environments, though these principles are useful across a variety of applications where coupling is required in environments with dynamic temperatures during operation. Considering cryosurgical systems as backdrop, though, these systems can be used for cryoablating target tissues (e.g., malignant tissues or tumors). Typically, such systems include one or more cryoprobes, one or more cryomedia (e.g., gases or fluids) sources and a controller. The cryomedia sources can supply gases such as argon, nitrogen, air, krypton, C02, CF4, xenon, and various other gases. As used herein, "cryomedia" can refer to any media (e.g., gases or fluids) that reaches low temperatures (e.g., below 170 Kelvin). In some non-limiting exemplary embodiments, the media can reach low temperatures (e.g., below 170 Kelvin) when pressurized to pressures greater than about 1000 psi (e.g., typically around 3500 psi) and permitted to undergo Joule-Thomson expansion, as will be described further below. The cryosurgical system can also include a controller having one or more sensors, flow meters, timers, analog/digital converters, wired or wireless communication modules, etc. Additionally, the controller can also regulate the flow rate, temperature, and pressure of cryomedia supplied to the cryoprobe.

Cryoablation is typically preceded by identifying the site requiring ablative treatment by employing an imaging technique such as x-ray, ultrasound, Computed Tomography (CT) or Magnetic Resonance Imaging (MRI). Cryoablation is then achieved by inserting one or more cryoprobes into the site requiring ablative treatment and then cooling cryoprobe tips of the inserted cryoprobes such that the tissues surrounding the cryoprobe tips are subjected to cryoablative temperatures, typically below 230 Kelvin (e.g., about −40° C.) or lower. This technique causes resulting cooled tissues to lose their functional and structural integrity, and in the case of cancerous cells, cease growing and multiplying.

During cryosurgery, for instance, a surgeon may deploy one or more cryoprobes to cryoablate a target area of a patient anatomy by placing the cryoprobe at or near the target area of the patient anatomy. In one example, a cryoprobe utilizes the Joule-Thomson effect to produce cooling or heating. In such cases, a cryomedia expands in the cryoprobe from a higher pressure to a lower pressure. Expansion of the cryomedia results in temperatures at or below those necessary for cryoablating a tissue in the vicinity of the tip of the cryoprobe. Heat transfer between the expanded cryomedia and the outer walls of the cryoprobe can be used to form an iceball, and consequently cryoablate the tissue.

FIG. 1 is a schematic of an MRI-guided cryosurgery system 10 according to a non-limiting exemplary embodiment. As illustrated here, the system 10 can include a magnet room 12 having an MRI scanner 14 with an MRI magnet 16 for accommodating a patient 20. The MRI magnet 16 can be of open or closed type and can include access ports to allow a surgeon to access the patient 20. The MRI magnet 16 can also have electrical connection lines 54 (illustrated by solid lines) and/or mechanical connection lines (illustrated by dashed lines) in FIG. 1 for connecting to various electrical, control, and/or cryoablation systems as will be described further below. The system 10 can also include a control room 22 electrically (and/or magnetically) isolated from the magnet room 12 (e.g., by electrical and/or magnetic isolation), and an equipment room 24. The system 10 may be used to image the patient 20 before insertion of surgical tools 32 to visualize patient areas of interest, such as a tumor or a patient cavity. Further, imaging may be performed during insertion to guide the surgical tool to the intended location inside the patient 20. Additionally, imaging may be performed after insertion and during surgery, as well as after surgery.

Continuing with FIG. 1, in a non-limiting exemplary embodiment, the connection lines 54, 62 may terminate in one or more surgical tools 32, such as cryoprobes insertable inside a patient 20. Accordingly, in some such examples, the system 10 may include a connection interface 30 placed inside the magnet room 12 to permit connection of one or more surgical tools 32, 34, 36 to other components of the cryoablation systems that may be placed outside the magnet room 12 (for instance, in a control room 22 or an equipment room 24). For instance, the system 10 may include electrical connection lines 54 and fluid connection lines 62 extending from the control room 22 to the magnet room 12 to operatively connect a control system 40 to the surgical tools 32. The connection interface 30 can, in some advantageous examples, be provided on a cart 50 (which may be stationary or mobile) positioned proximal to the magnet to permit a plurality of surgical tools 32 to be directly or indirectly (e.g., electrically and/or fluidly) connected to the control system 40 positioned outside the magnet room 12 (e.g., in the control room 22). In the illustrated embodiment, the cart 50 is a mobile cart 50. More details about the connection interface 30 will be discussed in more detail below in relation to FIG. 3.

Features of the electrical and fluid connections between the control system 40 and the surgical tools 32 will now be described with reference to FIG. 1. The control system 40 can be electrically connected to a junction box 52 located external to the magnet room 12 by way of a first set of electrical connection lines 54. Further, the junction box 52 can include a second set of electrical connection lines 56 to connect to electrical and/or imaging equipment 57 (such as an imaging router and electrical filters) located external to the magnet room 12 (for instance, within the equipment room 24). A third set of electrical connection lines 58 may connect the electrical and/or imaging equipment 57 to the connection interface 30 and/or mobile cart 50 located inside the magnet room 12. The junction box 52 can permit removable electrical connection between components in the magnet room 12 and components in the electrical and/or control rooms.

Referring still to FIG. 1, in some examples, the system 10 may be used to perform cryosurgical procedures (e.g., cryoablation). Accordingly, in some examples, the system 10 may include one or more cryomedia sources 60. The cryomedia source 60 can be a liquid or gas container that can provide a fluid at cryogenic temperatures and pressures to surgical tools 32 (e.g., cryoprobes). The cryomedia source 60 can be a cooling gas such as argon, nitrogen, air, krypton, CF4 xenon, or N2O. As noted above, some cryosurgical tools are cryoneedles, which may be connected to one or more cryomedia sources 60 (e.g., sources of fluid such as liquid nitrogen or gas such as Argon) for delivering cryomedia to the one or more cryosurgical tools. After cryomedia is supplied to the tip of a cryosurgical tool, it is forced under pressure through a Joule-Thomson orifice, which causes its tip to cool rapidly as the cryomedia expands.

As can be seen from FIG. 1, the cryomedia source 60 is positioned outside the magnet room 12 and is fluidly connectable to the control system 40 by way of a first set of fluid connection lines 62. The control system 40 in turn can be fluidly connected to the connection interface 30 and/or mobile cart 50 by way of a second set of fluid connection lines 64 and a third set of fluid connection lines 66. A fourth set of fluid connection lines 68 can fluidly connect the surgical tools 32 (e.g., cryoprobes) to the connection interface 30 and/or mobile cart 50. The fluid lines can be flexible and/or detachable and may include other fluid components to regulate pressure of fluid passing therethrough. Fluid from the cryomedia source 60 may thus be conveyed by the set of fluid connection lines 62, 64, 66 and 68 to the surgical tools 32. Optionally, the system 10 can include a fluid connection panel 70 electrically isolated from the magnet room 12 so as to permit fluid connections between components present in the magnet room 12 and those in the control room 22. Similarly, an electrical connection panel 72 can facilitate electrical connections between components present in the magnet room 12 and those in the control room 22 and/or electrical room. The system 10 illustrated also includes an MRI display 86 operatively coupled to the MRI scanner 14 and positioned within the magnet room 12 for displaying an image representative of an anatomical feature of a patient 20 so as to provide guidance to a surgeon during surgery.

Figure 2:
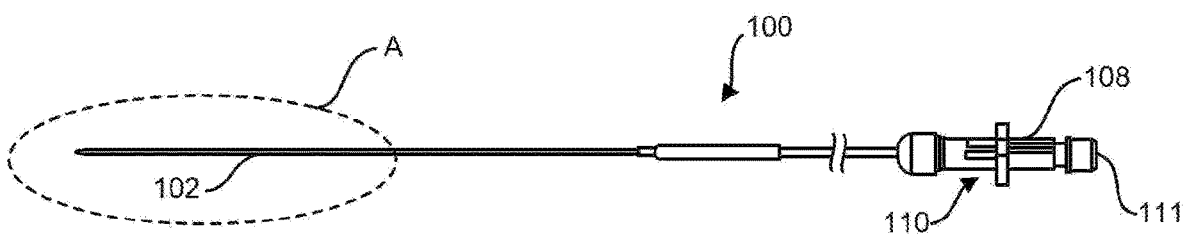
FIG. 2 is a plan view of a cryoprobe.
Figure 2A:
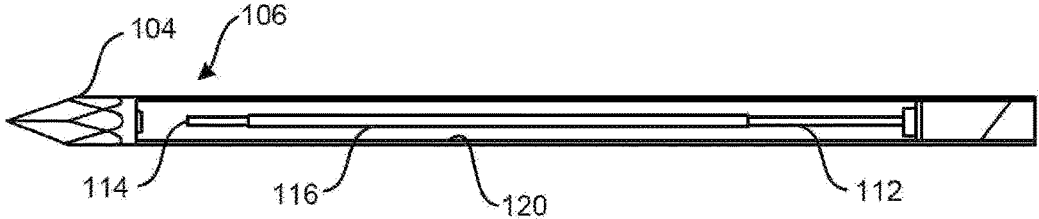
FIG. 2A is a sectional plan view of Detail A in FIG. 2A.

As described earlier, the surgical tool can be a cryoprobe 100 in a non-limiting exemplary embodiment. FIG. 2 is a front view of one such cryoprobe 100 and FIG. 2A is a sectional front view of the cryoprobe 100 of FIG. 2. Referring to FIGS. 2 and 2A, the cryoprobe 100 can include an elongate body. Components of the cryoprobe 100 can be located within a probe shaft 102. The cryoprobe 100 can, in some cases, be a cryoneedle, in which case, components of the cryoneedle may be arranged interior to a trocar. The probe shaft 102 can terminate in a distal operating tip 104 disposed at a distal section 106 of the cryoprobe 100 for penetrating through tissues of a patient 20 during deployment. For instance, in the illustrated example, the cryofluid supply tube 112 can terminate in a Joule-Thomson orifice 114. The Joule-Thomson orifice 114 can be positioned near the distal operating tip 104, so as to permit cryofluid exiting the Joule-Thomson orifice 114 to expand into an expansion chamber. In embodiments where the cryoprobe 100 is configured as a cryoneedle, the distal operating tip 104 can penetrate the patient's skin. In alternate embodiments, the cryoprobe 100 can be a flexible probe, and may be inserted by way of a catheter.

Cryosurgical tools such as cryoneedles can have a variety of connections. For instance, cryoneedles typically include a supply conduit for conveying cryomedia towards the Joule-Thomson orifice in the tip and a return conduit for evacuating cryomedia from the tip. Cryosurigcal systems may also include a feedback loop for recycling cryomedia being evacuated in the return conduit back into the supply conduit to convey it towards the tip again. Cryosurgical tools may also include a heater 116 in the tip enabling the cryosurgical tool to deliver a freeze-thaw cycle by alternately cooling the tip to cryogenic temperatures and then heating it up again. In some such examples, the lead wires, the terminal ends and the heater 116 wire may be bonded or otherwise attached to the cryofluid supply tube 112, and spaced apart from the inner surface 120 of the probe shaft 102 so as to electrically isolate the probe shaft 102 (which may be electrically conductive) from the current carrying heater 116. A proximal connector 108 can facilitate connections of the cryoprobe 100 to a connection interface 30, control system 40 and/or cryomedia source 60. Further, the proximal connector 108 can also have electrically conductive components (e.g., portions of proximal pin 111) so as to be in electrical communication with a corresponding probe shaft 102 (e.g., for use with the heater 116). These connections can terminate at a connector interface where connections can be made to a variety of sources.

A connector interface can provide one or more connections to supplies used by the cryosurgical tools. For instance, the connection interface 200 can include one or more electrical connections for coupling to the cryoneedle (e.g., at the proximal connector 108). In addition, or in alternative, the connection interface 200 can be used to connect the cryosurgical tools to the cryomedia source, for example, via a coupler. Cryosurgical systems typically incorporate one or more couplers. In a typical application, the coupler includes a male connector and a female connector for connecting a source of pressurized cryomedia to a cryosurgical tool to provide a fluid tight seal therebetween. The male connector and female connector used in cryosurgical systems are typically secured in place by a screw-in connector. Screw-in connectors have numerous disadvantages. For instance, they cannot be connected and disconnected quickly and sometimes the screwthreads on the male and female parts become cross threaded. Screw-in connectors also require additional tools such as a wrench to torque the connection down to ensure the connection is maintained under pressure. Principles of the present disclosure may prove advantageous to these typical applications and are described in more detail below.

FIG. 3 is a sectional front view of a portion of the connection interface 200 permitting connection of the cryoprobe of FIG. 2. This connection interface 200 can be similar to the connection interfaces discussed elsewhere herein, including the connection interface 30 discussed above. As noted there, this connection interface 200 can be provided inside the magnet room (e.g., via a mobile cart such as mobile cart 50 of FIG. 1) or another suitable connection location in the system. When the connection interface 200 is provided on the mobile cart 50, it is advantageously positionable within the magnet room (e.g., magnet room 12 of FIG. 1). The connection interface 200 includes housing portions in the form of a manifold 202 having a connection port 204 for connecting to a cryoprobe 100. The manifold 202 can include connection ports 204 in the form of recessed features formed in the manifold 202. As seen here, the manifold 202 includes a cryomedia supply line 209 and a cryomedia return line 211. In advantageous embodiments, the manifold 202 may include a single common cryomedia supply line 209 common to all connection ports 204. Alternatively, the manifold 202 may include two or more cryomedia supply lines. Each connection port 204 can be fluidly connected to the cryomedia supply line 209 such that cryomedia from the cryomedia source (e.g., cryomedia source 60 in FIG. 1) is conveyed by the first, second, third and fourth set of fluid connection lines (e.g., connection lines 62, 64, 66, 68 in FIG. 1) to the cryomedia supply line 209. In turn, the cryomedia supply line 209 supplies the cryomedia to the cryomedia supply tube (e.g., cryomedia supply tube 112 in FIG. 2A) of a cryoprobe connected to the corresponding connection port 204 and can be returned to the cryomedia source via cryomedia return line 211. Most notably, the connection interface 200 shown here differs from some discussed above because a coupler 220 according to principles of the present disclosure is provided therewith. More details about this coupler 220 are discussed below.

FIGS. 3A-3E show various features of couplers 220, according to principles of the present disclosure. In particular, FIG. 3A shows a view of the coupler 220. FIG. 3B shows a side view of a coupler 220 with multi-piece connectors. FIG. 3C shows a side view of a coupler 220 with a connected valve 326. FIG. 3D shows a side view of the coupler 220 in FIG. 3A with a clamp 332 to secure connectors of the coupler 220. FIG. 3E shows a side view of the coupler 220 in FIG. 3C with a clamp 332 to secure connectors of the coupler 220. As noted above, these couplers 220 can be used to advantageously couple cryosurgical tool to cryomedia sources. For instance, a cryosurgery system can include a cryosurgical tool having a cryogenic media supply conduit and a source of cryogenic media having a cryogenic media feed conduit. The cryogenic media feed conduit can be connectable to the cryogenic media supply conduit via a coupler 220. A coupler 220 according to principles of the present disclosure can connect the cryosurgical tool to the source of cryogenic media via coupling connections made to the cryogenic media supply line via one or more connectors that provide at least a fluid tight seal for operation.

Generally shown in these figures, a coupler 220 according to principles of the present disclosure can include a first sealing engagement and a second sealing engagement. This coupler 220 can be reusable as it is allowed to cycle through sealing stages while minimizing risks of detrimental deformation or damage experienced by typical coupler such as the screwtype couplers discussed above. The coupler 220 can have a formable flow path that occurs, for example, when connectors of the couplers 220 are secured together. The first sealing engagement can be configured to provide a first seal of the coupler 220 at a first temperature condition. The second sealing engagement can be configured to provide a second seal of the coupler 220 at a second temperature condition that is different from the first temperature condition. In examples, a working media (e.g., cryogenic media such as cryogenic liquids or gases) can be allowed to flow through the flow path. The first and second temperature conditions can be responsive to flow of the working media through the flow path. The cryosurgery system can include a heater that is configured to heat a portion of at least one of the first connector 310 and the second connector 320 such that the coupler 220 is configured to be thawed to release the first sealing engagement with operation of the heater.

Coupling connectors of the coupler 220 can facilitate formation of a flow path. For instance, the coupler 220 can include a first connector 310 and a second connector 320. The formable flow path can be formable via coupling of the first connector 310 with the second connector 320. In example, the first connector 310 can include a first fluid conduit, and the second connector 320 can include a second fluid conduit. The cryosurgery system can include a clamp 332 for securing the first and second connectors 310, 320 in a fluid-tight arrangement such that the first conduit 314 is in fluid communication with the second conduit 324 and a clamp locator (not shown) for locating the clamp 332 such that the first and second connectors 310, 320 are aligned. It is worth noting here that while discussed as having first and second connectors 310, 320, this disclosure should not be limited to interpretations that require only two connectors. To the contrary, this disclosure pertains to couplers 220 with multiple connectors Cryomedia can flow through the flow path formed by coupling the first connector 310 with the second connector 320. The flow path can be configured to receive the cryogenic media from the cryogenic media supply conduit. This cryomedia can flow through the coupler 220 and into the cryoneedle for use in the cryosurgery system. While flowing through the flow path, cryomedia will engage the first and second connectors 310, 320 and undergo heat exchange (e.g., cooling if using cryomedia).

Depending on the properties of the first and second connector 320, the first and second connectors 310, 320 will change over time as the cryomedia flows through the flow path. For instance, the first connector 310 can have a first coefficient of thermal expansion, and the second connector 320 can have a second coefficient of thermal expansion. The second coefficient of thermal expansion can be different from the first coefficient of thermal expansion. In this regard, physical characteristics (e.g., shape, area, volume, and density) of the first and second connectors 310, 320 can change relative to one another. When properly tuned according to principles of the present disclosure, these changes can result in sealing engagements made between the first and second connectors 310, 320. For instance, as explained further below, certain portions of the first and second connectors 310, 320 can be made to eliminate clearances therebetween as heat exchange occurs at the first and second connectors 310, 320.

Coefficients of thermal expansion can be selected such that the first and second connectors 310, 320 undergo changes at different rates during operation. In this regard, sealing engagements between the first and second connectors 310, 320 can be facilitated via thermal contraction or expansion of the first and second connectors 310, 320. The first coefficient of thermal expansion and the second coefficient of thermal expansion can be selected such that cooling causes first complementary surfaces of the first and second connectors 310, 320 to form the first sealing engagement. In examples, the first and second connectors 310, 320 can have different genders such that one is a male connector and the other is a female connector. In this regard, the first connector 310 can be configured to receive the second connector 320 such that under the first temperature condition an exterior surface of the first connector 310 engages an interior surface of the second connector 320 so as to form the first sealing engagement. In examples, the first sealing engagement is provided between first complementary surfaces of the first and second connectors 310, 320. In examples, the second sealing engagement can be provided between second complementary surfaces of the first and second connectors 310, 320. In examples, a resilient seal 330 can be provided between the second complementary surfaces. The second sealing engagement can be provided by a resilient seal 330 arranged between second complementary surfaces of the first and second connectors 310, 320.

So configured, the coupler 220 can perform as a temperature dependent two-stage sealing coupler 220. As previously noted, the first and second sealing engagements can respectively correspond to the first and second temperature conditions. These temperature conditions can be ranges of temperature experienced during operation. In addition, or in alternative, the first temperature condition can include a first range of temperatures, and the second temperature condition includes a second range of temperatures that is different from the first range of temperatures. Under these circumstances, as further discussed below, the first sealing engagement can occur at a different time than the second sealing engagement as the coupler 220 experiences cooling during cryosurgery operations. In examples, the first range of temperatures can be lower than the second range of temperatures. The first temperature condition can include a first range of temperatures that includes cryogenic temperatures such that the first sealing engagement is formed at the cryogenic temperatures. The second sealing engagement can occur at non-cryogenic temperatures and/or may abut or overlap with the first sealing engagement such that the coupler 220 is continuously sealed throughout operation. For instance, the first sealing engagement can occur only during the first temperature condition (e.g., a first engagement stage), and the second sealing engagement can occur only during the second temperature condition (e.g., a second engagement stage). More details about components in the coupler 220 are discussed below.

FIG. 3A shows a side view of a coupler 220 according to principles of the present disclosure. In the non-limiting example illustrated here, there are first and second connectors 310, 320 included in the coupler 220. A distal end 316 of the first connector 310 has a frustoconical portion 316a. The first connector 310 forms a sealing engagement with the second connector 320 to form at least a fluid tight engagement and places the first conduit 314 in fluid communication with the second conduit 324. The first connector 310 has a first connection element 312 with a first coefficient of thermal expansion and the second connector 320 has a second connection element 322 with a second coefficient of thermal expansion. A resilient seal 330 is provided between the first connector 310 and the second connector 320 and is configured to facilitate formation of a sealing engagement therebetween.

In more detail, the coupler 220 shown here is suitable for connecting a source of pressurized cryomedia to a cryosurgical tool. The coupler 220 includes a first connector 310 with a first coefficient of thermal expansion. The first connector 310 has an exterior surface and a first conduit 314 that is configured to allow passage of a cryomedia therethrough. The coupler 220 includes a second connector 320 with a second coefficient of thermal expansion. The second coefficient of thermal expansion is different to the first coefficient of thermal expansion. The second connector 320 includes an interior surface that is complementary to and adapted to receive the exterior surface of the first connector 310. The second connector 320 includes a second conduit 324 that is configured to allow passage of a cryomedia therethrough. A resilient seal 330 is configured to facilitate formation of a sealing engagement between the first connector 310 and the second connector 320. Coupling the first connector 310 to the second connector 320 forms a sealing engagement that is at least fluid tight and places the first conduit 314 in fluid communication with the second conduit 324. The first coefficient of thermal expansion and the second coefficient of thermal expansion are selected such that cooling the coupler 220 causes an exterior surface of the first connector 310 to form a sealing engagement (e.g., the first sealing engagement) against the interior surface of the second connector 320.

FIG. 3B shows a side view of a coupler 220 that includes a frustoconical portion 316a at the distal end 316 of the first connector 310. This coupler 220 can be similar to those couplers 220 discussed elsewhere herein. Of note here, the first connector 310 is formed of two separate pieces: a distal end portion 310a and the main body portion 310b (or barrel portion 310b). In this example, the distal end portion 310a is frustoconical in form.

According to principles of the present disclosure, as was the case with other couplers disclosed elsewhere herein, a multi-stage sealing engagement is provided between the first connector 310 and the second connector 320. For instance, as shown here in FIG. 3, the second connector 320 has an interior surface that is complimentary to and adapted to receive an exterior surface of the first connector 310 in an engaged arrangement. When the coupler 220 is first formed by bringing the first connector 310 into an engaged arrangement with the second connector 320, a sealing engagement (e.g., the second sealing engagement) between the first connector 310 and second connector 320 is provided by the resilient seal 330. Typically, the sealing engagement can first be formed at room temperature (typically between 18° C. and 24° C.). In examples, the resilient seal 330 can provide a reliable sealing engagement that is at least fluid tight through temperatures as low as −40° C. This can be a first stage of sealing engagement and can continue until or overlap with another sealing engagement that occurs in another stage.

Multi-stage sealing engagement can occur at different temperature ranges experienced during operation. As the coupler 220 is cooled (e.g., in use when cryomedia is being forced under high pressure through the coupler 220), the resilient seal 330 continues to form a sealing engagement between the first connector 310 and the second connector 320. As the first connector 310 and the second connector 320 have different coefficients of thermal expansion, however, these connectors experience thermal contraction at different rates. As noted above, the coefficients of thermal expansion of the first connector 310 and second connector 320 are selected such that cooling the coupler 220 causes the first connector 310 to form a sealing engagement with the second connector 320. In examples, this sealing engagement starts to be formed at temperatures where the fluid tight seal provided by the resilient seal 330 (e.g., the second sealing engagement) is still maintained. Due to the connectors being selected to have different coefficients of thermal expansion, upon cooling, one connector contracts more extensively over time compared to the other. This relationship causes gaps or clearances between the first and second connectors 310, 320 to reduce until they come into a sealing engagement with each other. This sealing engagement not only provides at least a fluid tight seal between the first connector 310 and the second connector 320 but also secures the two connectors together. In this regard, the sealing engagement can be reversed by allowing the coupler 220 to warm up to room temperature again. Thus, the need to use a wrench to torque the coupler 220 down to the required tension and to disconnect it again can be eliminated.

Temperature ranges can be a design consideration for the coupler 220. For instance, a sealing engagement can be maintained (albeit across multiple stages) between the first connector 310 and the second connector 320 over a large temperature range. At higher temperatures (for example at room temperature), this sealing engagement can be achieved by the resilient seal 330. At lower temperatures (e.g., during cooling), this sealing engagement can be achieved by the first connector 310 and second connector 320 coming into a secured arrangement with each other as a result of thermal contraction to form a fluid tight seal. For example, the resilient seal 330 may be formed from a material selected such that it is guaranteed to provide a fluid tight seal at temperatures as low as −40° C. At the same time, the relative thermal contraction between the first connector 310 and the second connector 320 results in a fluid tight seal being formed between the two connectors at temperatures below −10° C. In this example there is an overlapping range of temperatures between −40° C. and −10° C. where a fluid tight seal is provided by both mechanisms.

According to principles of the present disclosure, there can be designed couplers 220 that have an overlapping range of temperatures where fluid tight sealing engagements are provided by multiple mechanisms. When in use in a cryosurgery system, the coupler 220 is initially at room temperature (typically between 18° C. and 24° C.). As cryomedia is fed through the system (e.g., through the first and second conduits), the coupler 220 is cooled. The resilient seal 330 therefore provides a fluid tight seal initially (e.g., during the initial stages of cooling), and following that fluid tight seals are provided by both mechanisms in the overlapping temperature range. When the connection union is cooled to the extent that the material the resilient seal 330 is formed starts to deform (and thus is no longer able to maintain a fluid tight seal reliably) a sealing engagement is still maintained between the first connector 310 and the second connector 320 as a result of the relative thermal contraction. A fluid tight seal is therefore always provided between the first connector 310 and the second connector 320 across a wide temperature range.

Features of the first connector 310 in non-limiting examples will now be described. The first connector 310 has a first coefficient of thermal expansion and comprises a first conduit 314 connectable to either a cryosurgical tool or a source of cryomedia. The first connector 310 is brought into a connection union with the second connector 320 to place the first conduit 314 in fluid communication with the second conduit 324. In examples, the first connector 310 is a male connector (and therefore the second connector 320 is a female connector). In this regard, the male connector and the female connector can form a fluid tight seal. The male connector can include a coefficient of thermal expansion that is different to the coefficient of thermal expansion of the female connector. The male connector can include an exterior surface for receiving a resilient seal 330 where the exterior surface is complimentary to the internal surface of the female connector. The male connector can include a first conduit 314 that is connectable to either a cryosurgical tool or a source of cryomedia. The coefficient of thermal expansion of the male connector can be selected such that cooling causes the exterior surface of the male connector to form a fluid tight seal with the internal surface of the female connector.

Physical characteristics of the first connector 310 can facilitate sealing engagement with the second connector 320 during operation. For instance, the first connector 310 can be a male connector with a frustoconical portion 316a at the distal end 316. In this regard, the proximate end can connect to a cryosurgical tool or the source of cryomedia and the distal end 316 is the opposite end. Cooling can cause the exterior surface of the first connector 310 to form a fluid tight seal against the interior surface of the second connector 320 at least along a portion of the frustoconical portion 316a of the first connector 310. The frustoconical portion 316a may be formed from a separate piece to the remainder of the first connector 310 such that the first connector 310 comprises a frustoconical portion 316a and a separate main body (barrel) portion. Alternatively, the frustoconical portion 316a and the main body (barrel) portion may be integrally formed as a single piece.

Portions of the first connector 310 can have different coefficients of thermal expansion. For instance, the first connector 310 may include a first connection element 312 having a first coefficient of thermal expansion. In this regard, the first connection element 312 is a portion of the first connector 310 that interfaces with the second connector 320 and as such only this portion of the first connector 310 needs to be formed of material having a first coefficient of thermal expansion. Optionally the remainder of the first connector 310 may also be formed of material having a first coefficient of thermal expansion. In the example where the first connector 310 comprises a frustoconical portion 316a, the first connection element 312 can include the frustoconical portion 316a (or a part of the frustoconical portion 316a) and only this portion of the first connector 310 may be formed of a material having a first coefficient of thermal expansion. It is therefore optional whether the remaining part of the first connector 310 (for example the main body portion 310b) is formed from this same material having the first coefficient of thermal expansion.

At one's discretion, the first connector 310 can have a lower coefficient of thermal expansion than the second connector 320. In this example, the first connector 310 can include a material with a low coefficient of thermal expansion such that it undergoes relatively little contraction during cooling whereas the second connector 320 comprises a material that will contract more significantly when cooled. Upon cooling, this causes gaps or clearances between the first connector 310 and the second connector 320 to reduce in size until the first and second connectors 310, 320 come into a sealing engagement. This arrangement can provide at least fluid tight seal and can optionally be arranged to provide an airtight seal in some instances. In examples, the first connector 310 includes an alloy having between about 55% and 70% nickel and about 30% and 45% iron and, optionally, the first connector 310 comprises invar (FeNi36). Invar is a material that has a minimal coefficient of thermal expansion such that it barely contracts or expands when being cooled or warmed up.

When the first connector 310 comprises a frustoconical portion 316a at its distal end 316, only the frustoconical portion 316a of the first connector 310 (or a part thereof) may need to include an alloy having between about 55% and 70% nickel and about 30% and 45% iron and preferably this alloy is invar (FeNi36). In this embodiment the remainder of the first connector 310 may be formed from any other material suitable for being using in a cryoablation system, for example non-corrosive metals and alloys.

Features of the second connector 320 will now be discussed. In examples, the second connector 320 can have a second coefficient of thermal expansion. The second connector 320 can include a second conduit 324 that is connectable to a cryosurgical tool or a source of cryomedia. The second connector 320 can be coupled to the first connector 310 to place the second conduit 324 in fluid communication with the first conduit 314. The second connector 320 can have a second coefficient of thermal expansion that is optionally different from the coefficient of thermal expansion of the first connector 310.

When the second connector 320 is a female connector, the first connector 310 can be a male connector. In this regard, a female connector for coupling to a male connector to form a fluid tight seal is disclosed. This female connector can include a coefficient of thermal expansion that is different from the coefficient of thermal expansion of the male connector. The female connector can include an interior surface that is complimentary to the external surface of the male connector. The female connector can include a (second) conduit that is configured to be in fluid communication with either a cryosurgical tool or source of cryomedia. The coefficient of thermal expansion of the female connector can be selected such that cooling causes the exterior surface of the male connector to form a fluid tight seal with the internal surface of the female connector.

Portions of the second connector 320 can have different coefficients of thermal expansion. The second connector 320 can optionally include a second connection element 322 having a second coefficient of thermal expansion. In examples, the second connection element 322 is a portion of the second connector 320 that interfaces with the first connector 310. In this regard, only this portion of the second connector 320 may be formed of material having a second coefficient of thermal expansion. Optionally the remainder of the second connector 320 may be formed of a material having a second coefficient of thermal expansion. When the first connector 310 includes a frustoconical portion 316a. The second connection element 322 can include a portion of the second connector 320 that interfaces with the frustoconical portion 316a of the first connector 310. In this regard, only this portion of the second connector 320 may need to be formed of a material having a second coefficient of thermal expansion. It is therefore optional whether the remaining part of the second connector 320 is formed from this same material having the second coefficient of thermal expansion.

At one's discretion, the second connector 320 can include a material having a higher coefficient of thermal expansion than the first connector 310. In this example, the second connector 320 can include a material selected to exhibit a greater rate of contraction during cooling than the material selected for the first connector 310. For instance, the second connector 320 can include an alloy that has iron and carbon and optionally steel. For example, the second connector 320 can include stainless steel 300 series that is particularly suitable for use in a cryoablative environment because it is non-corrosive.

Features of the first and second conduits will now be discussed. Starting with the first conduit 314, it can be connectable to either a cryosurgical tool or a source of cryomedia. The first conduit 314 can be configured to allow passage of a cryomedia. When the coupler 220 is used in a cryosurgery system the first conduit 314 can be connected to either a cryosurgical tool or a source of cryomedia. In this regard, where the first conduit 314 is connected to a cryosurgical tool the second connector 320 can be connected to the source of cryomedia and vice versa. In examples, the first conduit 314 can be integrally formed within the first connector 310. Alternatively, the first conduit 314 can be formed from a separate piece to the first connector 310 such that the first connector 310 is able to move freely along the first conduit 314 coaxially with the first conduit 314 as the first connector 310 has an internal channel.

Regarding the second conduit 324, in examples, it is connectable to either a cryosurgical tool or a source of cryomedia. In this regard, the second conduit 324 can be configured to allow passage of a cryomedia. When the coupler 220 is used in a cryosurgery system, the second conduit 324 can be arranged such that it is connected to either a cryosurgical tool or a source of cryomedia. When the first conduit 314 is connected to a cryosurgical tool, the second connector 320 can be connected to the source of cryomedia and vice versa. In an embodiment of the invention, the second conduit 324 is integrally formed within the second connector 320. Alternatively, the second conduit 324 is formed from a separate piece to the second connector 320 and in this embodiment the second connector 320 is able to move freely along the second conduit 324 coaxially with the second conduit 324 as the second connector 320 has an internal channel.

FIG. 3C shows a side view of a coupler 220 according to principles of the present disclosure. As shown here, the coupler 220 includes a frustoconical portion 316*a* at the distal end 316 of the first connector 310, and the second connector 320 includes a valve 326. The first connector 310 includes an extension 318 beyond the frustoconical portion 316*a* at the distal end 316 of the first connector 310 such that the first connector 310 is configured to open the valve 326 upon connection of the first connector 310 with the second connector 320 in a sealing engagement. Upon opening the valve 326 the first conduit 314 is brought into fluid communication with the second conduit 324. The valve 326 shown here in FIG. 3 is a ball-and-socket valve 326 with a ball 326*a* and a socket 326*b*. In this regard, the valve 326 may open to allow the passage of fluid only when the sealing engagement is made. Under these circumstances, when used in a cryosurgery system the system does not need to be depressurized as the coupler 220 can be connected and disconnected when the system is under pressure.

Features of the resilient seal 330 will now be described. As alluded to above, the resilient seal 330 is provided for forming a sealing engagement between the first connector 310 and the second connector 320. The resilient seal 330 is formed from a material that is able to provide a sealing engagement to temperatures well below about 0° C., and optionally at temperatures as low as about –40° C. A sealing engagement is maintained by the resilient seal 330 until the material thereof becomes insufficiently resilient to provide the sealing engagement. In examples, this phenomenon begins to occur when the coupler 220 is cooled to about –40° C. At and below these temperatures, however, a sealing engagement (e.g., the first sealing engagement) will already be provided by the first connector 310 forming a fluid tight seal against the interior surface of the second connector 320 due to the two connectors comprising materials having different coefficients of thermal contraction.

Temperatures at which the first connector 310 and second connector 320 will form a sealing with each other depends on the selected materials. In examples, these materials will be selected such that a sealing is formed at temperatures of –10° C. and below. As such, the materials of the resilient seal 330, the first connector 310, and the second connector 320 may be selected such that there is an overlapping temperature range where sealing engagement of the coupler 220 is provided by both the resilient seal 330 and the relative contraction of the two connectors. This overlapping temperature range can be between about –10° C. and about –40° C. In examples, the resilient seal 330 is an elastomeric resilient seal 330 and optionally is formed from a fluoropolymer such as silicone. In examples, the resilient seal 330 is an o-ring seal. In examples, the resilient seal 330 is provided on the first connector 310 prior to the connection union being formed. In this regard, after the first connector 310 is coupled to the second connector 320, the resilient seal 330 can be in contact with both the first connector 310 and the second connector 320 (e.g., such that the second sealing engagement is formed).

Features of the heater will now be discussed. In examples, as noted above, a heater (not shown) is provided and is configured to heat a portion of the first connector 310 and/or second connector 320. In this regard, the heater can be used to release the sealing engagement between the first and second connectors 310, 320 (e.g., between the exterior surface of the first connector 310 and the interior surface of the second connector 320). When the coupler 220 is used in a cryoablation system, it is cooled to cryoablative temperatures around –160° C. or lower. At these temperatures, sealing engagement between the first and second connectors 310, 320 is which maintained at least as a result of the relative thermal contraction rates of the two connectors. When the cryoablation procedure is completed, the connection union will warm up to room temperature, and eventually the sealing engagement between the first connector 310 and the second connector 320 will be released albeit fairly slowly. Incorporating a heater so configured can heat a portion of the first connector 310 and/or the second connector 320 to speed up the warming process so that the coupler 220 can be quickly disconnected at the end of a cryoablation procedure.

FIGS. 3D and 3E show various features of clamps according to principles of the present disclosure. As will be described in more detail below, the clamps are useful with the couplers 220 disclosed elsewhere herein. FIG. 3D shows a side cross-sectional view of a coupler 220 with a frustoconical portion 316*a* at the distal end 316 of the first connector 310 with a clamp 332 for securing the first connector 310 and second connector 320 in a sealing engagement such that the first conduit 314 is in fluid communication with the second conduit 324. FIG. 3E shows a side cross-sectional view of a coupler 220 with a frustoconical portion 316*a* at the distal end 316 of the first connector 310. The second connector 320 includes a valve 326, and the first connector 310 includes an extension 318 beyond the frustoconical portion 316*a* at the distal end 316 of the first connector 310. So arranged, the extension 318 is configured to open the valve 326 upon coupling of the first connector 310 with the second connector 320 to form a sealing engagement. Further illustrated is a clamp 332 for securing the first connector 310 and second connector 320 together in sealing engagement such that the first conduit 314 is in fluid communication with the second conduit 324.

In more detail, the coupler 220 shown in FIG. 3D is has the first connector 310 including a frustoconical portion 316*a* at its distal end 316 and further includes a clamp 332. The clamp 332 is configured to secure the first connector 310 and the second connector 320 together in a sealing engagement where the first conduit 314 is in fluid communication with the second conduit 324. The coupler 220 illustrated here further includes a spring-loaded push fit system 334 to ensure a tight connection between the first connector 310 and the second connector 320. Optionally an actuating lever (not shown) is also incorporated to correctly locate the clamp 332.

The coupler 220 shown in FIG. 3E shows the first connector 310 including a frustoconical portion 316*a* at its distal end 316 and the second connector 320 including a valve 326. The first connector 310 can include an extension 318 beyond the frustoconical portion 316*a*. As with FIG. 3D, FIG. 3E shows the coupler 220 including a clamp 332 and a spring-loaded push fit system 334. While not illustrated here, as discussed below, there are examples of the coupler 220 where there is a clamp 332 without a spring-loaded push fit system 334.

While discussed above in relation to cooling applications, heating compliant examples are also contemplated. In this regard, the coupler 220 and related principles discussed above (and elsewhere herein) can be applied to heating applications as well. For instance, the first and second coefficients of thermal expansion can be selected such that the first and second connectors 310, 320 progress into sealing engagement as the connector is heated (e.g., by sending heating media through the first and second conduits).

Whether cooling or heating compliant, the coupler 220 can benefit from a disposable cover (not shown) to mitigate damage from use. For instance, repeated use of the first and second connectors 310, 320 can cause wear between complementary surfaces thereof. As such, the disposable cover can be designed to cover these surfaces, such as frustoconical portions 316a and/or main body portions 316b of the first and second connectors 310, 320. In an example, the disposable cover is designed to cover one or more complementary surfaces of the first connector 310 while in other examples, the disposable cover is designed to cover one or more complementary surfaces of the second connector 320. Such disposable covers can comprise soft, compliant metal with lower yield point than that of the first and/or second connectors 320. In this regard, the disposable cover can be deformable and thereby facilitate forming a seal between the first and second connectors 310, 320. For example, in cooling applications, the disposable cover can comprise copper or similar metals and, in heating applications, the disposable cover can comprise gold or similar metals. These are just some examples of many examples.

Features of the clamp 332 will now be discussed with respect to FIGS. 3D and 3E. Inserting the first connector 310 into the second connector 320 to form a sealing engagement can initially bring the first conduit 314 into fluid communication with the second conduit 324. While the resilient seal 330 is able to provide a sealing engagement between the first connector 310 and the second connector 320, additional measure may be required to securely hold the coupler 220 in place, particularly when the coupler 220 is used in a cryosurgical system under pressure. Optionally, a push fit system 334 is used when the first connector 310 and second connector 320 are brought together to form a sealing engagement. Using a push fit system 334 can ensure a sealing connection that is strong enough to withstand pressure above atmospheric pressures and can eliminate the need for screwing one connector into the other. The push fit system 334 can be a spring-loaded push fit system 334 that provides an enhanced insertion force. Optionally, the push fit system 334 is secured in place by a clamp 332 that allows the connection union to withstand even higher pressures without being forced apart. For a particularly secure sealing engagement, the push fit system 334 can be a spring-loaded push fit system 334 that is secured by the clamp 332. The inclusion of either a spring-loaded push fit system 334, a clamp 332, or both, ensures a consistent insertion force is applied after the first connector 310 is inserted into the second connector 320 to form the sealing engagement.

In more detail, the clamp 332 can be configured to secure (e.g., couple) the first connector 310 and the second connector 320 in a sealing engagement. Under these circumstances, the first conduit 314 can be in fluid communication with the second conduit 324. Incorporating a clamp 332 into the coupler 220 can ensure the first connector 310 and the second connector 320 are secured in sealing engagement (e.g., when they are first couple together). When the coupler 220 is at room temperature, the resilient seal 330 can provide a sealing engagement only between the first connector 310 and the second connector 320. Thus, incorporating a clamp 332 ensures that the two connectors are secured together as well as having a sealing engagement therebetween. This arrangement can be particularly useful when the coupler 220 is used in a cryoablative system during the initial stages of cooling. At this point, there may have been insufficient thermal contraction in the first connector 310 and the second connector 320 for the two connectors to be in a sealing engagement. In this regard, certain examples of the coupler 220 may have the clamp 332 in lieu or in addition to the resilient member. When the coupler 220 is formed with a spring-loaded push fit system 334, the clamp 332 can be fixed in place over the coupler 220. Of course, in examples, the clamp 332 can comprise multiple discrete pieces that together form the clamp 332. In some examples, the clamp 332 is another mechanical-type clamp such as a screw clamp or lever clamp.

Particularly useful may be a feature for locating the clamp 332. As such, the coupler 220 can include a locator (not shown) for correctly locating the clamp 332 such that the first connector 310 and second connector 320 are aligned to ensure that the first conduit 314 is in fluid communication with the second conduit 324. In particular, the locator for correctly locating the clamp 332 is an actuating lever. For instance, this actuating lever can be configured to insert the first connector 310 into the second connector 320 (or vice versa). This insertion can be include exerting a force (directly or indirectly) onto one or both of the connectors 310, 320. In other examples, the lever can be more of a guide that guides one connector into engagement with the other connector. These examples are just some of many examples of the lever.

FIG. 4 shows a flowchart of a method 400 for coupling surgical tools, according to principles of the present disclosure. Such methods can be useful for coupling a source of cryogenic fluid to a cryosurgical tool using a coupler. As shown here, the method 400 can include at step 410 sealing the coupler with a first seal via a first sealing engagement that is configured to provide the first seal of the coupler at a first temperature condition. Step 420 of the method 400 can include causing a temperature change in the coupler. Step 430 of the method 400 can include sealing the coupler with a second seal via a second sealing engagement that is configured to provide the second seal of the coupler at a second temperature condition that is different from the first temperature condition. Step 440 of the method 400 can include directing the coupler to come to come to a temperature at which the coupler can be uncoupled. In examples, the method 400 can include clamping the first and second connectors in a fluid-tight arrangement such that a first conduit of the first connecter is in fluid communication with a second conduit of the second connector.

Sealing the coupler can be a multi-stage process. In examples, sealing the coupler with the first seal via the first sealing engagement that is configured to provide the first seal of the coupler at the first temperature condition can include allowing first complementary surfaces of first and second connectors to move into sealing engagement. The first connector can have a first coefficient of thermal expansion and the second connector can have a second coefficient of thermal expansion that is different from the first coefficient of thermal expansion. In examples, sealing the coupler with the second seal via the second sealing engagement that is configured to provide the second seal of the coupler at the second temperature condition that is different from the first temperature condition can include forming a fluidic seal between second complementary surfaces of the first and second connectors.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cryosurgery system comprising a cryosurgical tool having a cryogenic media supply conduit and a source of cryogenic media having a cryogenic media feed conduit connectable to the cryogenic media supply conduit via a coupler with a formable flow path, the coupler comprising:
    a first sealing engagement that is configured to provide a first seal of the coupler at a first temperature condition;
    a second sealing engagement that is configured to provide a second seal of the coupler at a second temperature condition that is different from the first temperature condition;
    a first connector having a first coefficient of thermal expansion; and
    a second connector having a second coefficient of thermal expansion that is different from the first coefficient of thermal expansion; and
    wherein the formable flow path is formable via coupling of the first connector with the second connector such that a working media is allowed to flow through the flow path and the first and second temperature conditions correspond to the flow of the working media through the flow path.

2. The cryosurgery system of claim 1, wherein the first sealing engagement is provided between first complementary surfaces of the first and second connectors.

3. The cryosurgery system of claim 2, wherein the second sealing engagement is provided between second complementary surfaces of the first and second connectors.

4. The cryosurgery system of claim 3, wherein a resilient seal is provided between the second complementary surfaces.

5. The cryosurgery system of claim 2, wherein the first connector is configured to receive the second connector such that under the first temperature condition an exterior surface of the first connector engages an interior surface of the second connector so as to form the first sealing engagement.

6. The cryosurgery system of claim 1, wherein the first temperature condition includes a first range of temperatures, and the second temperature condition includes a second range of temperatures that is different from the first range of temperatures.

7. The cryosurgery system of claim 6, wherein at least one of: the first range of temperatures is lower than the second range of temperatures and the first range of temperatures has minimal overlap with the second range of temperatures.

8. The cryosurgery system of claim 7, wherein the first range of temperatures includes cryogenic temperatures.

9. The cryosurgery system of claim 1, wherein the first connector is coupleable to the second connector via a clamping force such that the formable flow path is configured to withstand high-pressure operating conditions.

10. A cryosurgery system comprising a cryosurgical tool having a cryogenic media supply conduit and a source of cryogenic media having a cryogenic media feed conduit connectable to the cryogenic media supply conduit via a coupler comprising:
    a first sealing engagement that is configured to provide a first seal of the coupler at a first temperature condition;
    a second sealing engagement that is configured to provide a second seal of the coupler at a second temperature condition that is different from the first temperature condition;
    a first connector having a first coefficient of thermal expansion; and
    a second connector having a second coefficient of thermal expansion that is different from the first coefficient of thermal expansion; and
    wherein a flow path of the coupler is formable via engagement of the first connector with the second connector, the flow path being configured to receive the cryogenic media from the cryogenic media supply conduit.

11. The cryosurgery system of claim 10, wherein the first temperature condition comprises a first range of temperatures that includes cryogenic temperatures such that the first sealing engagement is formed at the cryogenic temperatures; and wherein the cryosurgery system further comprises a heater that is configured to heat a portion of at least one of the first connector and the second connector such that the coupler is configured to be thawed to release the first sealing engagement with operation of the heater.

12. The cryosurgery system of claim 10, wherein the first coefficient of thermal expansion and the second coefficient of thermal expansion are selected such that cooling causes first complementary surfaces of the first and second connectors to form the first sealing engagement; and wherein the second sealing engagement is provided by a resilient seal arranged between second complementary surfaces of the first and second connectors.

13. The cryosurgery system of claim 10, wherein the first connector comprises a first fluid conduit and the second connector comprises a second fluid conduit, and wherein the cryosurgery system further comprises a clamp for securing the first and second connectors in a fluid-tight arrangement such that the first conduit is in fluid communication with the second conduit and a clamp locator for locating the clamp such that the first and second connectors are aligned.

14. A method of coupling a source of cryogenic fluid to a cryosurgical tool using a coupler, the method comprising:
    sealing the coupler with a first seal via a first sealing engagement that is configured to provide the first seal of the coupler at a first temperature condition and
    sealing the coupler with a second seal via a second sealing engagement that is configured to provide the second seal of the coupler at a second temperature condition that is different from the first temperature condition;
    wherein sealing the coupler with the first seal via the first sealing engagement that is configured to provide the first seal of the coupler at the first temperature condition includes allowing first complementary surfaces of first and second connectors to move into sealing engagement, wherein the first connector has a first coefficient of thermal expansion and the second connector has a second coefficient of thermal expansion that is different from the first coefficient of thermal expansion.

15. The method of claim 14, wherein sealing the coupler with the second seal via the second sealing engagement that is configured to provide the second seal of the coupler at the second temperature condition that is different from the first temperature condition includes forming a fluidic seal between second complementary surfaces of the first and second connectors.

16. The method of claim 15, further comprising clamping the first and second connectors in a fluid-tight arrangement such that a first conduit of the first connector is in fluid communication with a second conduit of the second connector.

17. The cryosurgery system of claim 1, wherein the first temperature condition comprises a first range of temperatures that includes cryogenic temperatures such that the first sealing engagement is formed at the cryogenic temperatures; and wherein the cryosurgery system further comprises a heater that is configured to heat a portion of at least one of the first connector and the second connector such that the coupler is configured to be thawed to release the first sealing engagement with operation of the heater.

18. The method of claim 15, wherein the first temperature condition comprises a first range of temperatures that includes cryogenic temperatures such that the first sealing engagement is formed at the cryogenic temperatures; the method further comprising heating a portion of at least one of the first connector and the second connector with a heater such that the coupler is configured to be thawed to release the first sealing engagement with operation of the heater.

* * * * *